United States Patent
Tanaka et al.

(10) Patent No.: US 8,486,722 B1
(45) Date of Patent: Jul. 16, 2013

(54) SENSING METHOD FOR BIOPOLYMERS AND SENSING DEVICE THEREFOR

(71) Applicants: Saburo Tanaka, Toyohashi (JP); Shinji Katsura, Toyohashi (JP); Noriyuki Ohnishi, Ichihara (JP); Kageaki Matsui, Ichihara (JP)

(72) Inventors: Saburo Tanaka, Toyohashi (JP); Shinji Katsura, Toyohashi (JP); Noriyuki Ohnishi, Ichihara (JP); Kageaki Matsui, Ichihara (JP)

(73) Assignees: National University Corporation Toyohashi University of Technology, Toyohashi-shi (JP); JNC Corporation, Tokyo (JP)

( * ) Notice: Subject to any disclaimer, the term of this patent is extended or adjusted under 35 U.S.C. 154(b) by 0 days.

(21) Appl. No.: 13/713,643

(22) Filed: Dec. 13, 2012

Related U.S. Application Data

(62) Division of application No. 11/686,025, filed on Mar. 14, 2007, now Pat. No. 8,372,659.

(30) Foreign Application Priority Data

Mar. 17, 2006 (JP) .................................. 2006-074219

(51) Int. Cl.
*G01N 33/553* (2006.01)
*G01N 33/543* (2006.01)

(52) U.S. Cl.
USPC .......................................... 436/526; 436/518

(58) Field of Classification Search
USPC ................................................. 436/518, 526
See application file for complete search history.

(56) References Cited

U.S. PATENT DOCUMENTS

| | | | |
|---|---|---|---|
| 6,123,902 | A | 9/2000 | Koch et al. |
| 6,995,558 | B2 | 2/2006 | Butters et al. |
| 7,695,905 | B2 | 4/2010 | Furukawa et al. |
| 7,981,688 | B2 | 7/2011 | Stayton et al. |
| 2005/0175702 | A1 | 8/2005 | Muller-Schulte |

FOREIGN PATENT DOCUMENTS

| | | |
|---|---|---|
| JP | 11-68180 | 3/1999 |
| JP | 2001-133458 | 5/2001 |
| JP | 2004-61144 | 2/2004 |
| JP | 2004-157072 | 6/2004 |

*Primary Examiner* — Mark Shibuya
*Assistant Examiner* — Pensee Do
(74) *Attorney, Agent, or Firm* — Oblon, Spivak, McClelland, Maier & Neustadt, L.L.P.

(57) ABSTRACT

A sensing method for biopolymers by detecting the magnetic signal generated from a labeled biopolymer under AC magnetic field with thermo-responsive magnetic nano particles as label having a critical solution temperature across which the particles have the ability to aggregate or disperse with cooling or heating.

5 Claims, 5 Drawing Sheets

SENSING METHOD FOR BIOPOLYMERS AND SENSING DEVICE THEREFOR

BACKGROUND OF THE INVENTION

1. Field of the Invention

Present invention relates to a sensing method for biopolymers and a sensing device therefor.

2. Description of the Related Art

In the investigation of biotechnology, it becomes frequently necessary to prepare a large amount of a particular antigen, although the preparation of the antigen generally requires a great deal of labor, time and expenses. However, a marked reduction in time and expenses required for the purification of the antigen becomes possible with the use of the monoclonal antibody which specifically binds with the antigen. For example, if we inject an antigen into an animal such as mouse, a corresponding antibody is formed in the body whereas the antibody forming cell dies out. Accordingly, an immortalized antibody forming cell (hybridoma), which has been prepared by cell fusion techniques, is conventionally used in the purification of the said antigen. However, there are various kinds of hybridomas, and it is necessary to select the hybridoma which specifically recognizes the target antigen to form monoclonal antibody.

In the selection process, a plurality of small containers (wells) in which the antigen is pre-adhered are prepared, the solutions of monoclonal antibody produced by hybridoma are pipetted into them, and then the quantity of reacted monoclonal antibody is examined in each well. Conventionally, the determination of the quantity is carried out by means of fluorescent or radioactive labeling. In the said conventional fluorescent labeling method, however, the accuracy of the estimation is lowered due to the fluorescent fading, so called bleaching phenomenon, thus the estimation should be carried out in a short time. The use of radioactive labeling is also undesirable from the viewpoint of safety measure, since the use of radioactive ray is limited in a specified controlled area and the risk for radiation exposure of operator should be considered.

As for the sensing devices for antigen antibody reaction, the present inventors have proposed devices detecting the magnetic signals with high sensitivity by means of a superconducting quantum interference device (SQUID) magnetic sensor, in which AC magnetic field is imposed on the antibody labeled with magnetic fine particles with several microns in diameter in the course of the antigen antibody reaction (for example, see patent documents 1 and 2). In addition, a method to impose DC magnetic field has been also proposed (for example, see patent documents 3 and 4). Although these methods have partly solved above described drawbacks, the sensitivity of the detection is not sufficient yet.

[Patent document 1] Japanese unexamined patent application publication no. 2001-133458

[Patent document 2] Japanese unexamined patent application publication no. 2004-061144

[Patent document 3] Japanese unexamined patent application publication no. 11-068180

[Patent document 4] Japanese unexamined patent application publication no. 2004-157072

In light of the foregoing, it is an object of the present invention to provide a highly sensitive sensing method for biopolymers and a sensing device therefor, by amplifying the magnetic signal generated from the biopolymer reaction using the thermo-responsive magnetic nano particles.

SUMMARY OF THE INVENTION

In order to achieve above described object, the present invention provides the following:

[1] The present invention provides a sensing method for biopolymers by detecting magnetic signals generated from a labeled biopolymer under AC magnetic field with the use of the thermo-responsive magnetic nano particles as label. The method is characterized by using the thermo-responsive magnetic nano particles having a critical solution temperature across which the particles have the ability to aggregate or disperse with cooling or heating, binding a ligand for a target biopolymer to the thermo-responsive magnetic nano particles, labeling the biopolymer in solution with the thermo-responsive magnetic nano particles bound with the ligand using a biopolymer reaction, adding ligand free thermo-responsive magnetic nano particles, keeping the solution temperature at which the thermo-responsive magnetic nano particles aggregate, applying AC magnetic field after aggregating the thermo-responsive magnetic nano particles and enlarging the aggregate of the thermo-responsive magnetic nano particles, and obtaining a larger magnetic signal at the time of measurement as compared with the signal obtained when the ligand free thermo-responsive magnetic nano particles are not added.

[2] The sensing method for biopolymers described in above [1] is characterized by binding an antibody for a target antigen to the thermo-responsive magnetic nano particles, labeling the antigen in solution with the thermo-responsive magnetic nano particles bound with the antibody using an antigen antibody reaction, adding thermo-responsive magnetic nano particles which are not bound with antibody, keeping the solution temperature at which the thermo-responsive magnetic nano particles aggregate, applying AC magnetic field after aggregating the thermo-responsive magnetic nano particles and enlarging the aggregate of the thermo-responsive magnetic nano particles, obtaining a larger magnetic signal at the time of measurement as compared with the magnetic signal obtained when the thermo-responsive magnetic nano particles, which are not bound with antibody, are not added, and finally detecting the antigen.

[3] The sensing method for biopolymers described in above [1] is characterized by labeling a single stranded DNA complementary to a target single stranded DNA with the thermo-responsive magnetic nano particles, hybridizing the complementary DNA with the target single stranded DNA in solution, adding the thermo-responsive magnetic nano particles which are not labeled with single stranded DNA just before the measurement of magnetic signals, keeping the solution temperature at which the thermo-responsive magnetic nano particles aggregate, applying AC magnetic field after aggregating the thermo-responsive magnetic nano particles and enlarging the aggregate of the thermo-responsive magnetic nano particles, obtaining a larger magnetic signal at the time of measurement as compared with the magnetic signal obtained when the thermo-responsive magnetic nano particles, which are not bound with the complementary DNA, are not added, and finally detecting the target single stranded DNA.

[4] In the sensing method for biopolymers described in any one of above [1] to [3], the thermo-responsive magnetic nano particles comprise a thermo-responsive polymer and magnetic nano particles, wherein the thermo-responsive polymer is the polymer having a lower critical solution temperature or an upper critical solution temperature and the magnetic nano particles are the particles comprising a polyhydric alcohol and a magnetic material. The polymer having a lower critical solution temperature is the polymer comprising at least one monomer component which is selected from the group consisting of N-n-propylacrylamide, N-isopropylacrylamide, N-ethylacrylamide, N,N-dimethylacrylamide, N-acryloylpyrrolidine, N-acryloylpiperidine, N-acryloylmorpholine, N-n-propylmethacrylamide, N-isopropylmethacrylamide, N-ethylmethacrylamide, N,N-dimethylmethacrylamide, N-methacryloylpyrrolidine, N-methacryloylpiperidine, and N-methacryloylmorpholine. The polymer having an upper critical solution temperature is the polymer comprising at least one monomer component which is selected from the group consisting of acrylamide, acetylacrylamide, biotinol acrylate, N-biotinyl-N'-methacryloyltrimethyleneamide, N-acryloylglycinamide, acryloylsarcosinamide, methacryloylsarcosinamide, acryloylnipecotamide, and acryloylmethyluracil. The polyhydric alcohol is at least one alcohol component which is selected from the group consisting of dextran, polyvinyl alcohol, mannnitol, and sorbitol, and the magnetic material is at least one kind of material which is selected from the group consisting of oxide magnetic materials and metallic magnetic materials.

[5] The sensing device of the present invention is characterized by (a) means for binding thermo-responsive magnetic nano particles having a critical solution temperature across which the particles have the ability to aggregate or disperse with cooling or heating to a ligand for the target biopolymer, and labeling the biopolymer in solution with the thermo-responsive magnetic nano particles bound with the ligand using a biopolymer reaction, (b) means for adding ligand free thermo-responsive magnetic nano particles before the measurement of the magnetic signal which is performed after the biopolymer reaction, (c) means for aggregating the thermo-responsive magnetic nano particles and enlarging the aggregate of the thermo-responsive magnetic nano particles by keeping the above described added thermo-responsive magnetic nano particles at the temperature at which the thermo-responsive magnetic nano particles aggregate, (d) a sliding mechanism by which the biopolymer labeled with the above described aggregated and enlarged thermo-responsive magnetic nano particles is transferred, (e) a device for the application of AC magnetic field to said biopolymer, (f) a cryostat, and (g) a SQUID magnetic sensor arranged in the vicinity of the biopolymer and located above said cryostat, wherein (h) a larger magnetic signal from above described biopolymer at the time of measurement is obtained as compared with magnetic signal obtained when the ligand free thermo-responsive magnetic nano particles are not added.

[6] The sensing device for biopolymers described in above [5] is characterized by binding antibody for target antigen to said thermo-responsive magnetic nano particles, labeling the antigen with the thermo-responsive magnetic nano particles bound with the antibody using an antigen antibody reaction in solution, adding the thermo-responsive magnetic nano particles which are not bound with antibody, keeping the solution temperature at which the thermo-responsive magnetic nano particles aggregate, applying AC magnetic field after aggregating the thermo-responsive magnetic nano particles and enlarging the aggregate of the thermo-responsive magnetic nano particles, obtaining a larger magnetic signal at the time of measurement as compared with the magnetic signal obtained when the thermo-responsive magnetic nano particles, which are not bound with antibody, are not added, and finally detecting the antigen antibody reaction.

[7] The sensing device for biopolymers described in above [5] is also characterized by binding a ligand for a target biopolymer to the thermo-responsive magnetic nano particles, labeling a single stranded DNA with the thermo-responsive magnetic nano particles bound with the ligand in solution, adding the thermo-responsive magnetic nano particles which are not bound with the ligand, keeping the solution temperature at which the thermo-responsive magnetic nano particles aggregate, applying AC magnetic field after aggregating the thermo-responsive magnetic nano particles and enlarging the aggregate of thermo-responsive magnetic nano particles, obtaining a larger magnetic signal at the time of measurement as compared with the magnetic signal obtained when the ligand free thermo-responsive magnetic nano particles is not added, and finally detecting the DNA hybridization.

[8] In the sensing device for biopolymers described in any one of above [5] to [7], the thermo-responsive magnetic nano particles comprise a thermo-responsive polymer and magnetic nano particles, wherein the thermo-responsive polymer is the polymer having a lower critical solution temperature or an upper critical solution temperature and the magnetic nano particles are the particles comprising a polyhydric alcohol and a magnetic material. The polymer having a lower critical solution temperature is the polymer comprising at least one monomer component which is selected from the group consisting of N-n-propylacrylamide, N-isopropylacrylamide, N-ethylacrylamide, N,N-dimethylacrylamide, N-acryloylpyrrolidine, N-acryloylpiperidine, N-acryloylmorpholine, N-n-propylmethacrylamide, N-isopropylmethacrylamide, N-ethylmethacrylamide, N,N-dimethylmethacrylamide, N-methacryloylpyrrolidine, N-methacryloylpiperidine, and N-methacryloylmorpholine. The polymer having an upper critical solution temperature is the polymer comprising at least one monomer component which is selected from the group consisting of acrylamide, acetylacrylamide, biotinol acrylate, N-biotinyl-N'-methacryloyltrimethyleneamide, N-acryloylglycinamide, acryloylsarcosinamide, methacryloylsarcosinamide, acryloylnipecotamide, and acryloylmethyluracil. The polyhydric alcohol is at least one alcohol component which is selected from the group consisting of dextran, polyvinyl alcohol, mannnitol, and sorbitol, and the magnetic material is at least one kind of material which is selected from the group consisting of oxide magnetic material and metallic magnetic material.

[9] In the sensing method for biopolymers described in above [4], the thermo-responsive magnetic nano particles comprise a thermo-responsive polymer and magnetic nano particles, the thermo-responsive polymer comprising the polymer obtained from N-isopropylacrylamide or from N-acryloylglicinamide, and the magnetic nano particles are the particles comprising dextran and ferrite.

[10] In the sensing device for biopolymers described in above [8], the thermo-responsive magnetic nano particles comprises a thermo-responsive polymer and magnetic nano particles, the thermo-responsive polymer comprising the polymer obtained from N-isopropylacrylamide or from N-acryloylglicinamide, and the magnetic nano particles are the particles comprising dextran and ferrite.

DESCRIPTION OF THE PREFERRED EMBODIMENTS

Figure 1:
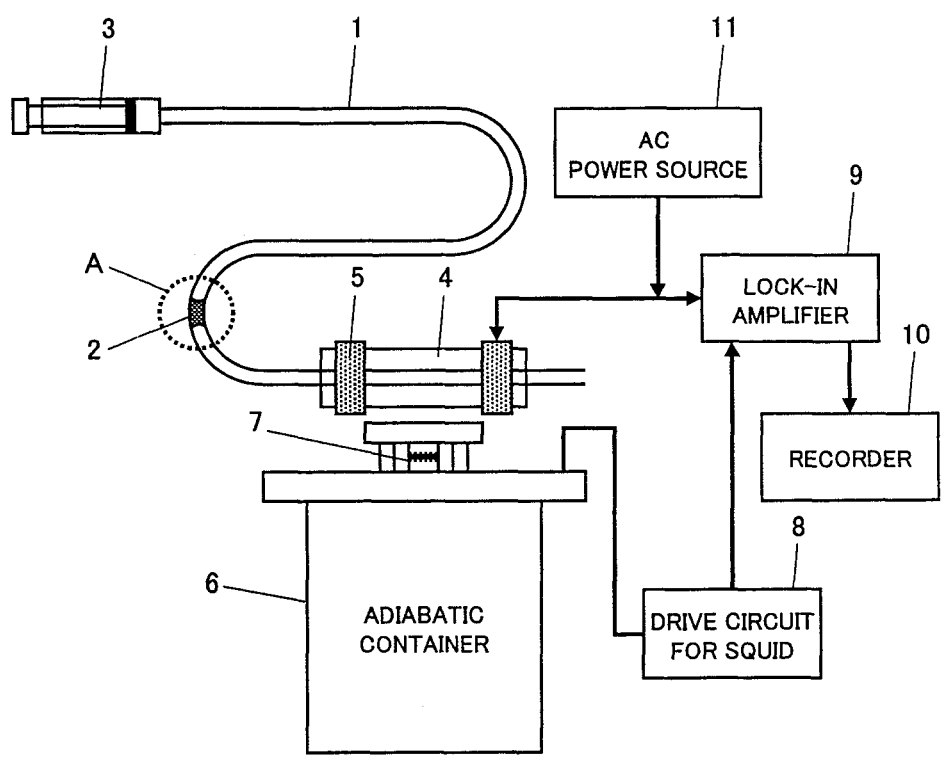
FIG. 1 is a configuration diagram of the sensing device for the detection of antigen antibody reaction in accordance with the first embodiment of the present invention.

The present invention comprises the method for detecting biopolymers by measuring an amplified magnetic signal generated from the reaction of labeled biopolymer under AC magnetic field using thermo-responsive magnetic nano particles as label. This method includes steps of binding a ligand for a target biopolymer to the thermo-responsive magnetic nano particles having a critical solution temperature across which the particles have the ability to aggregate or disperse with cooling or heating, labeling the biopolymer in solution with the thermo-responsive magnetic nano particles bound with the ligand using a biopolymer reaction, adding ligand free thermo-responsive magnetic nano particles, keeping the solution temperature at which the thermo-responsive magnetic nano particles aggregate, applying AC magnetic field after aggregating the thermo-responsive magnetic nano particles and enlarging the aggregate of the thermo-responsive magnetic nano particles, and obtaining a larger magnetic signal at the time of measurement as compared with the magnetic signal obtained when the ligand free thermo-responsive magnetic nano particles are not added. The ligand free thermo-responsive magnetic nano particles are added just before the measurement of the magnetic signal and the excess quantity of addition is prefarable, about 1.1 to 5 times of the quantity of the thermo-responsive magnetic nano particles bound with the ligand.

In the present invention, the temperature of aggregation of the thermo-responsive magnetic nano particles is below an upper critical solution temperature (abbreviated hereinafter as UCST) when the thermo-responsive magnetic nano particles have an upper critical solution temperature, while the temperature of aggregation of the thermo-responsive magnetic nano particles is above a lower critical solution temperature (abbreviated hereinafter as LCST) when the thermo-responsive magnetic nano particles have a lower critical solution temperature.

The thermo-responsive magnetic nano particles used in the present invention have the structure that a thermo-responsive polymer is bound to magnetic nano particles. The thermo-responsive polymer is characterized either by aggregating or by dispersing with heating or cooling across the critical solution temperature of the thermo-responsive polymer. Magnetic nano particles are those particles showing the magnetism with the particle diameter of nm sizes. The magnetic signal generated from these magnetic nano particles under AC magnetic field is weak when the particles are dispersed in an aqueous solution. The magnetic nano particles bound with the thermo-responsive polymer (referred as the thermo-responsive magnetic nano particles), however, become the aggregated state when the temperature is changed by cooling or heating into the temperature range where the aggregation of the particles occurs. When AC magnetic field is imposed in this aggregated state, the magnetic signal generated from the aggregate of the thermo-responsive magnetic nano particles is amplified and enhanced.

In the present invention, both polymers having an upper critical solution temperature and having a lower critical solution temperature can be used as the thermo-responsive polymer. Here, the wording "having an upper critical solution temperature" means the characteristic property of the polymer to aggregate due to the structural change taking place below a critical solution temperature when the temperature is lowered. On the other hand, the wording "having a lower critical solution temperature" means the characteristic property of the polymer to aggregate due to the structural change taking place above a critical solution temperature when the temperature is raised.

In the present invention, the biopolymers to be detected include DNA, RNA, antigens, antibodies, vitamins, and enzymes or the like. In order to detect these biopolymers, it is necessary to bind specific species (ligand) to the thermo-responsive magnetic nano particles developed by the present invention and to form specific site for the binding of target biopolymer. For example, in the case that the target biopolymer is a single stranded DNA, the ligand with which the DNA hybridizes is another single stranded DNA complementary to the target single stranded DNA. In the case that the target biopolymer is biotin, the ligand is avidin. In the case that the target biopolymer is an antibody, the ligand is an antigen. Further, it is possible to bind fluorescent probes to these ligands.

In the present invention, the biopolymer reaction means the binding reaction of the ligand being bound to the thermo-responsive magnetic nano particles with the target biopolymer, and more concretely, includes antigen antibody reaction, and hybridization reaction or the like.

The thermo-responsive magnetic nano particles used in the present invention comprises a thermo-responsive polymer and magnetic nano particles, and the application of the thermo-responsive magnetic nano particles may be further possible by binding the ligands. The thermo-responsive magnetic nano particles include a thermo-responsive polymer and magnetic nano particles, the thermo-responsive polymer is the polymer having a lower critical solution temperature or an upper critical solution temperature, and the magnetic nano particles is the particles comprising a polyhydric alcohol and magnetic particles.

The polymer having a lower critical solution temperature used in the present invention is the polymer comprising at least one monomer component which is selected from the group consisting of N-n-propylacrylamide, N-isopropylacrylamide, N-ethylacrylamide, N,N-dimethylacrylamide, N-acryloylpyrrolidine, N-acryloylpiperidine, N-acryloylmorpholine, N-n-propylmethacrylamide, N-isopropylmethacrylamide, N-ethylmethacrylamide, N,N-dimethylmethacrylamide, N-methacryloylpyrrolidine, N-methacryloylpiperidine, and N-methacryloylmorpholine, and preferably the polymer consisting of N-isopropylacrylamide.

The polymer having an upper critical solution temperature used in the present invention is the polymer comprising at least one monomer component which is selected from the group consisting of acrylamide, acetylacrylamide, biotinol acrylate, N-biotinyl-N'-methacryloyltrimethyleneamide, N-acryloylglycinamide, acryloylsarcosinamide, methacryloylsarcosinamide, acryloylnipecotamide, and acryloylmethyluracil, and preferably the polymer consisting of N-acryloylglycinamide.

The polyhydric alcohol used in the present invention are at least one kind of alcohol which is selected from the group consisting of dextran, polyvinyl alcohol, mannnitol, and sorbitol, and preferably dextran.

The magnetic material used in the present invention is at least one kind of material which is selected from the group consisting of oxide magnetic materials and metallic magnetic materials. As for oxide magnetic materials, iron oxides such as ferrite, and 3d and 4f oxide groups of the periodic table may be used, and particularly iron oxides are preferably used. As for metallic magnetic materials, Fe, Co, Ni and 4f metal group of the periodic table may be used, and particularly Co is preferably used.

The thermo-responsive magnetic nano particles having an upper critical solution temperature used in the present invention can be prepared, for example, by the procedure shown hereinafter.

The magnetic nano particles (40 nm) can be prepared by the following procedure.

3 ml of the aqueous mixture of ferric chloride hexahydrate (1.0 M) and ferrous chloride tetrahydrate (0.5 M) and 60 ml of 10 wt. % aqueous solution of a polyhydric alcohol, dextran (Wako Pure Chemicals Industries Ltd., molecular weight 32000 to 40000), were introduced in a 100 ml flask. After being stirred by a mechanical stirrer and raised the temperature to 50° C., 5.0 ml of 25 wt. % ammonia solution was added dropwise, and stirred further for about 1 hr. The magnetic nano particles with average diameter of ca. 40 nm fixed with dextran were obtained by this procedure.

The thermo-responsive magnetic nano particles having an upper critical solution temperature are prepared, for an example, by the following procedure.

1 ml of the thermo-responsive magnetic nano particles (40 nm sizes) having been prepared by the above described procedure were added to 15 ml of the 10 mM sodium carbonate solution. After being stirred for 2 hrs, 100 mg of glycidyl methacrylate was added and reacted for 72 hrs. After dialysis, the reaction mixture was concentrated to obtain methacrylated magnetic nano particles. 200 mg of N-acryloylglicinamide, 2 mg of above described methacrylated magnetic nano particles, and 3 mg of biotin monomer were introduced in a 50 ml three necked flask and the volume of the solution was adjusted to 20 ml by distilled water. After the solution was substituted with nitrogen gas, 30 mg of ammonium persulfate was added and reacted for 2 hrs at 50° C. to obtain the thermo-responsive magnetic nano particles having an upper critical solution temperature. The average diameter of the particles was about 100 nm (determined by light scattering photometer). The particles had an UCST at 20° C., aggregated in a solution below UCST, and could be easily recovered by a magnet. Upon heating the solution above UCST, the particles immediately dispersed and could not be easily recovered.

The thermo-responsive magnetic nano particles having a lower critical solution temperature are prepared, for example, by the following procedure.

300 mg of N-isopropylacrylamide, 3 mg of prepared biotin monomer, and 2 ml of 2 wt. % magnetic nano particles (40 nm) were introduced in a 50 ml three necked flask, and the solution was adjusted to 20 ml by distilled water. After the solution was substituted with nitrogen gas, 200 μl of 0.2 M ammonium cerium (IV) nitrate solution was added and reacted with stirring for 2 hrs to obtain the thermo-responsive magnetic nano particles having a lower critical solution temperature. The average diameter of these particles was about 100 nm (determined by light scattering photometer). The particles had an LOST at 37° C., perfectly dispersed in a solution below LOST, and could not be easily recovered by a magnet. Upon heating the solution above LOST, the particles immediately aggregated and could be easily recovered.

EMBODIMENTS

Embodiment of the present invention are illustrated in detail hereinafter.

Figure 2:
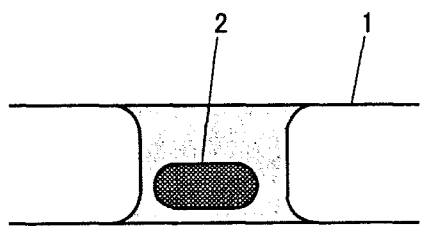
FIG. 2 is an enlarged figure of the part A of the sensing device for the detection of antigen antibody reaction shown in FIG. 1.

FIG. 1 is a configuration diagram of the sensing device for the detection of antigen antibody reaction in accordance with the first embodiment of the present invention, and FIG. 2 is an enlarged figure of the part A of the sensing device for the detection of antigen antibody reaction shown in FIG. 1.

In these figures, reference numeral 1 denotes a sample tube, 2 denotes the sample, 3 denotes a syringe pump, 4 denotes a supporting cylinder, 5 denotes a Helmholtz coil supported by both ends of supporting cylinder 4, 6 denotes an adiabatic container. Reference numeral 7 denotes a SQUID magnetic sensor arranged in the vicinity of the supporting cylinder 4 and located above the adiabatic container 6, 8 denotes a drive circuit for SQUID, 9 denotes a lock-in amplifier, 10 denotes a recorder, and 11 denotes an AC power source connected with the Helmholtz coil 5 and the lock-in amplifier 9.

Next, the measurement using the thermo-responsive magnetic nano particles having an upper critical solution temperature is illustrated.

Figure 3:
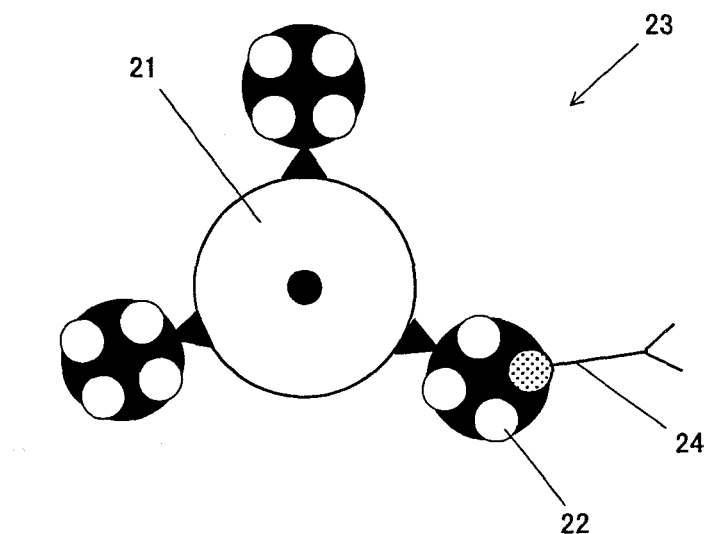
FIG. 3 is a schematic figure of a thermo-responsive nano particle in accordance with the first embodiment of the present invention.
Figure 4:
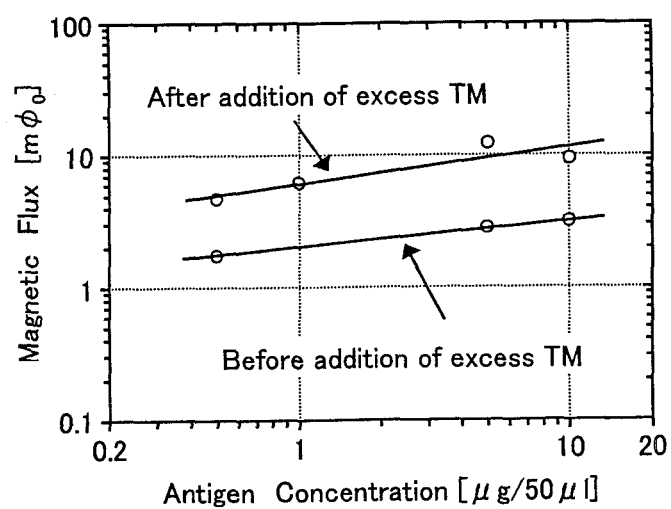
FIG. 4 is a characteristic figure showing the magnetic flux $(m\phi_0)$ as determined from magnetic signal plotted against the antigen concentration (μg/50 μl) in accordance with the first embodiment of the present invention.

For the measurement of said thermo-responsive magnetic nano particles, an AC magnetic field method was applied wherein the measurement was carried out by a SQUID magnetic sensor 7 keeping the imposition of AC magnetic field with a Helmholtz coil 5 to the sample 2. Sample 2 was prepared by fixing 0.005 to 10 μg/50 μl of an antigen, myosin, on a PCR (Polymerase Chain Reaction) plate, and then by reacting primary antibody, antimyosin. As shown in FIG. 3, on the surface of a thermo-responsive magnetic nano particle 21, avidin molecules 22 were bound to give a thermo-responsive magnetic nano particle with a 100 nm diameter 23, the particle was bound and labeled with biotinylated secondary antibody 24, and then the labeled particles were added to each PCR plate and reacted. 14 μl of the thermo-responsive magnetic particles 23 and 1 μl of secondary antibody 24 each of which has the concentration of 1 mg/1 ml were used in the reaction. Firstly, the magnetic signal only from the thermo-responsive magnetic nano particles labeled with antibody 23 was measured under the magnetic field of 0.45 mT (tesla) at 100 Hz. As a result, it was possible to detect the antigen concentration up to 4 μg/50 μl. Next, 50 μl of 0.1 mg/ml thermo-responsive magnetic nano particles were added, aggregated by cooling at 2° C., and washed out the excess thermo-responsive magnetic nano particles. After that, the magnetic signal was measured again under the same condition, and it has been recognized that the signal was enhanced about 3 to 4 times of magnitude as shown in FIG. 4. In FIG. 4, horizontal axis is the antigen concentration (μg/50 μl), and vertical axis is the magnetic flux ($m\phi_0$) as the measure of the magnetic signal. The measurement in the case of the thermo-responsive magnetic nano particles having a lower critical solution temperature may be carried out by a similar method as that described above. In the present invention, "TM" denotes the thermo-responsive magnetic nano particles.

Next, the method of detection of DNA hybridization using a single stranded DNA is illustrated in accordance with the second embodiment of the present invention.

Figure 5:
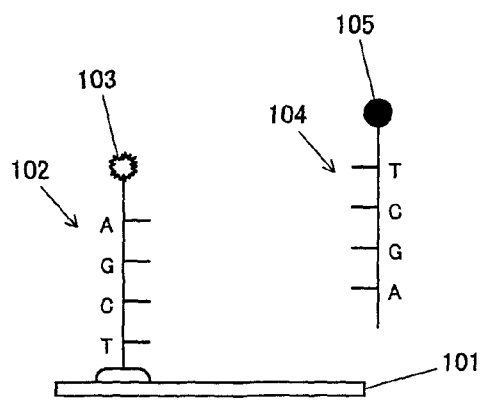
FIG. 5 shows the principle for detecting a biopolymer with the use of a thermo-responsive nano particle as a comparative example.

FIG. 5 shows the principle for detecting a biopolymer with the use of a thermo-responsive nano particle as a comparative example.

As shown in this figure, a target single stranded DNA 102 was fixed on an aldehyde coated substrate 101, and after having been recognized that the single stranded DNA 102 was labeled using Cy3 fluorescent label 103, sample DNA fragment 104 labeled with a magnetic nano particle 105 (core diameter 11 nm) was hybridized and the measurement of magnetic properties was carried out by means of a SQUID magnetic sensor with ultra high sensitivity as described below. As a result, it was recognized that the magnetic signal increased in proportion to the quantity of sample DNA with the addition of sample DNA fragment 104.

The thermo-responsive magnetic nano particles having an upper critical solution temperature related to the present invention is illustrated below.

The thermo-responsive magnetic nano particles having an upper critical solution temperature used in the present invention can be obtained from Magnabeat Inc. The aggregation of these thermo-responsive magnetic nano particles fully completed at about 10° C.

Figure 6:
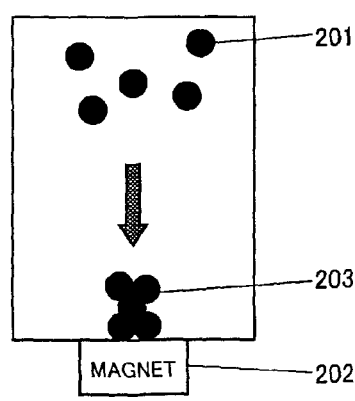
FIG. 6 shows the case in which magnetic micro particles (several μm sizes) are used as a comparative example.
Figure 7:
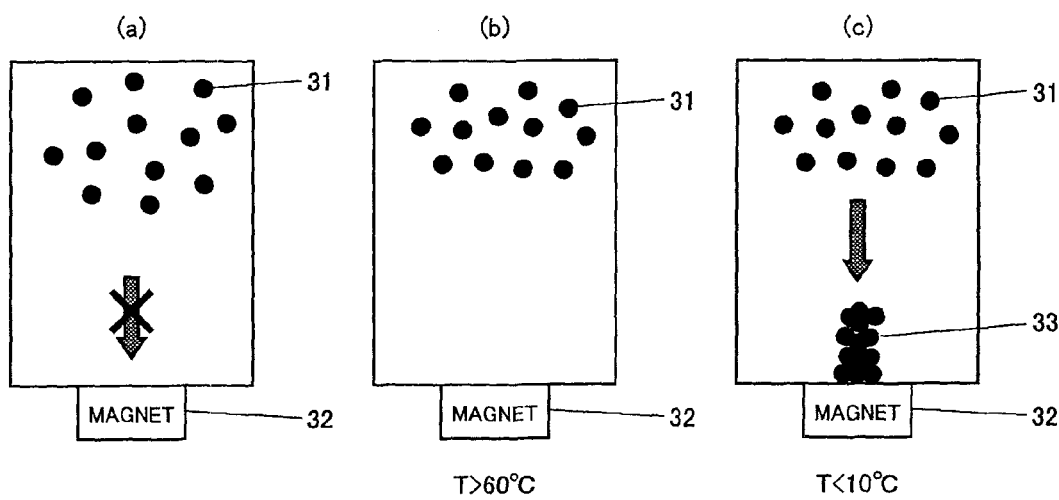
FIG. 7 depicts the illustration showing the characteristic feature of thermo-responsive nano particles having an upper critical solution temperature in accordance with the second embodiment of the present invention.

FIG. 6 shows the case in which magnetic micro particles (several μm sizes) are used as a comparative example, and these magnetic micro particles (several μm sizes) 201 was attracted by a magnet to form a large aggregated mass 203, while in the case that the sizes of the thermo-responsive magnetic particles were reduced to nano sizes as shown in FIG. 7(a), a thermo-responsive magnetic nano particle 31 showed the characteristics of super paramagnetism to lose remanent magnetism and not being attracted by a magnet 32. The thermo-responsive magnetic nano particles, however, can be designed, for example, so as to aggregate to form a large aggregated mass 33 at temperatures below 10° C. as shown in FIG. 7(c), while temperature above 60° C. to disperse finely with nano sizes to show the characteristic feature of super paramagnetism as shown in FIG. 7(b). The aggregated mass 33 showed an inherent ferromagnetism being attracted by a magnet 32, and had a large remanent magnetism. In the present invention, the aqueous dispersion of the thermo-responsive magnetic nano particles attached with avidin was prepared and the particles were bound to the biotinylated single stranded sample of DNA fragment.

Figure 8:
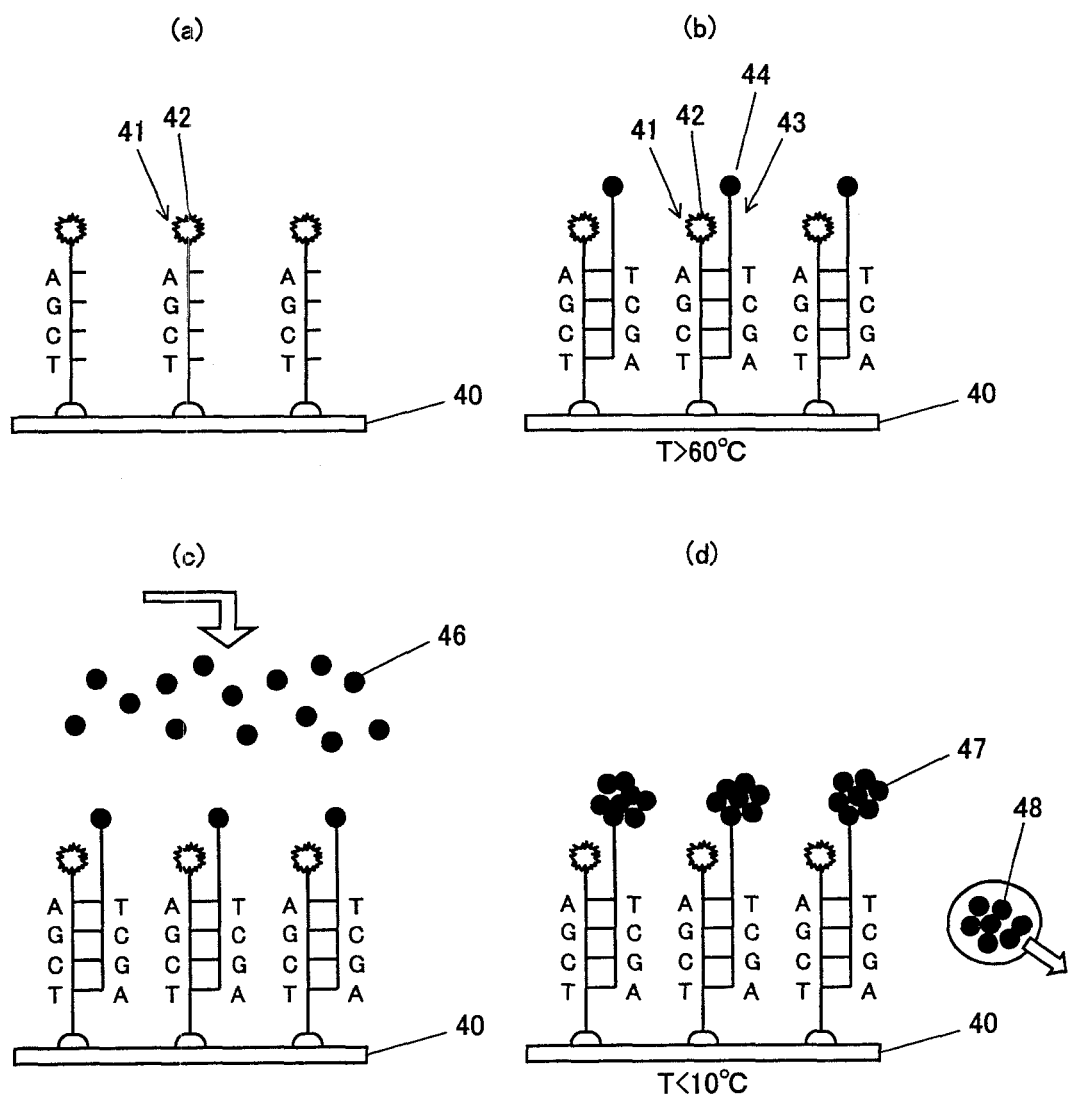
FIG. 8 is the schematic picture showing the principle for detecting biopolymer in accordance with the second embodiment of the present invention.

FIG. 8 is the schematic picture showing the principle for detecting biopolymer in accordance with the second embodiment of the present invention.

As shown in FIG. 8(a), a probe single stranded DNA 41 labeled with Cy3 fluorescent label 42 was fixed on a substrate 40, and the fixation of DNA was identified with a fluorescent microscope. Next as shown in FIG. 8(b), the sample DNA fragment 43 labeled with a thermo-responsive nano particle 44 was hybridized at the reaction temperatures of the solution above 60° C. Then as shown in FIG. 8(c), the thermo-responsive nano particles 46 without labeling by the DNA fragment were added. Next as shown in FIG. 8(d), the thermo-responsive nano particles were finally aggregated by lowering the temperature below 10° C. By using this procedure, the thermo-responsive magnetic nano particles labeled with DNA fragment 44 were enlarged to form a large aggregated mass 47 of the magnetic nano particles. Moreover, the aggregated unbound single stranded DNA fragment and excess floating thermo-responsive magnetic nano particles 48 were recovered by a magnet, and only the mass of the bound thermo-responsive magnetic nano particles was magnetized with a magnet. In this case, the thermo-responsive nano particles was in the form of enlarged and aggregated mass 47 of magnetic nano particles showing a ferromagnetism and a large remanent magnetism is maintained for over several hours. The substrate of a sample of the aggregated and enlarged mass of the thermo-responsive magnetic nano particles bound with DNA was transferred on the SQUID magnetic sensor described below and the magnetic signal was detected.

Another characteristic feature of the present invention is that the unbound single stranded DNA fragment and the excess thermo-responsive magnetic nano particles 48 is possible to be removed and recovered. This is a significant advantage because the washing process of the particles becomes unnecessary.

The measurement using the thermo-responsive magnetic nano particles having a lower critical solution temperature may also be carried out by the similar method described above.

Figure 9:
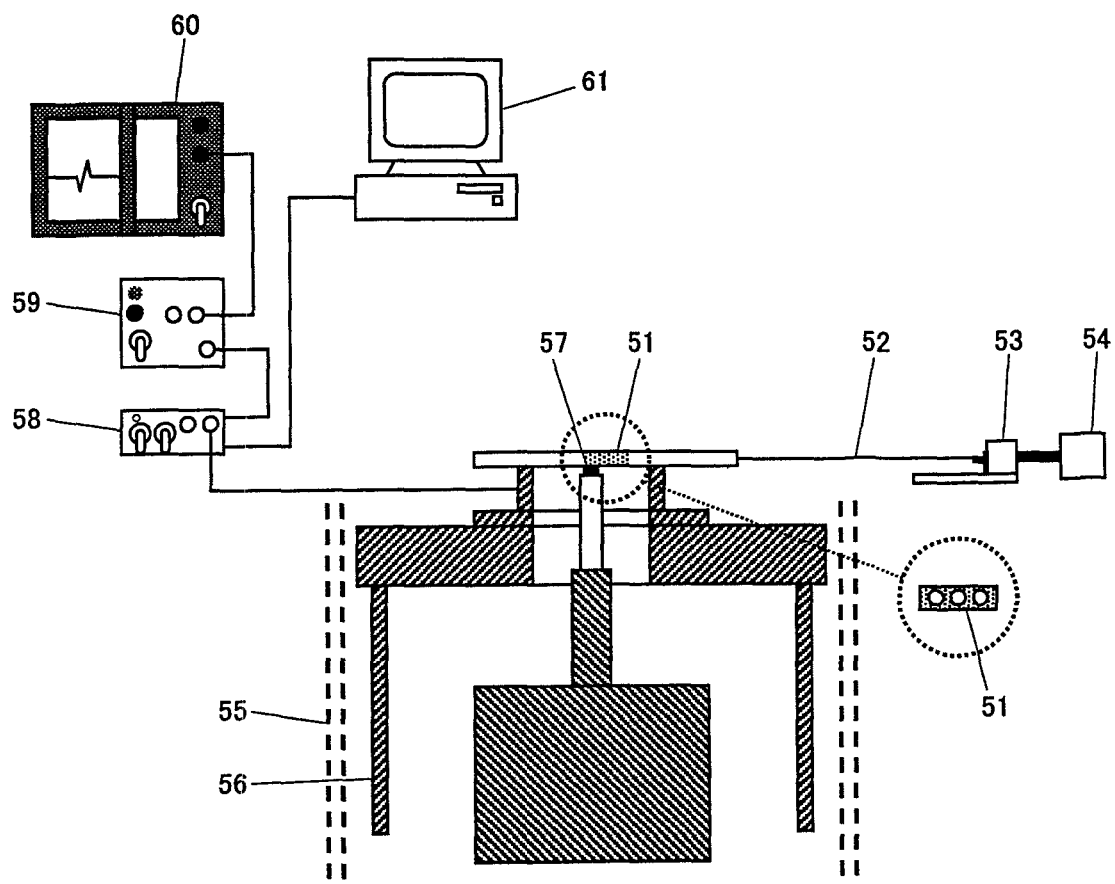
FIG. 9 is a schematic configuration diagram of the measuring system in accordance with the second embodiment of the present invention.
Figure 10:
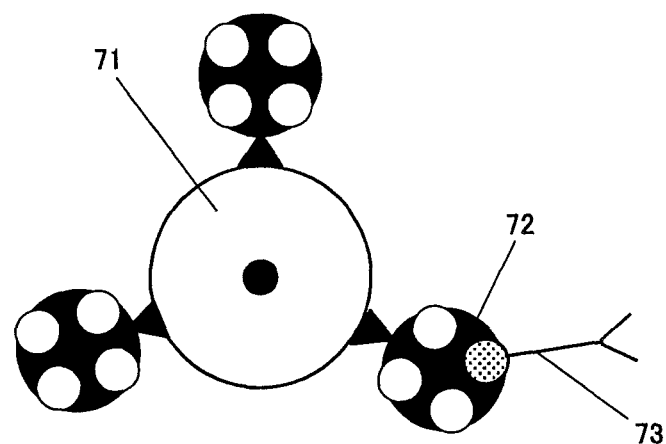
FIG. 10 is the schematic picture of a thereto-responsive magnetic nano particle having iron oxide or Co (cobalt) metal as a core.

FIG. 9 is a schematic configuration diagram of the measuring system in accordance with the second embodiment of the present invention. The device for the application of AC magnetic field on the sample is omitted in this diagram of the measuring system.

In this figure, reference numeral 51 denotes a sliding plate on which the single stranded DNA labeled with aggregated and enlarged thermo-responsive nano particles is loaded as a biopolymer sample, 52 denotes a wire, 53 denotes a driving motor, 54 denotes a control unit, 55 denotes a cryostat (a container keeping the temperatures low), 56 denotes a magnetic shield box, 57 denotes a SQUID (ultra high sensitive) magnetic sensor arranged in the vicinity of the sliding plate 51 and located above the cryostat 55, 58 denotes a drive circuit, 59 denotes an amplifier, 60 denotes an X-Y pen recorder, and 61 denotes a personal computer.

The measuring system comprises, (1) a SQUID (ultra high sensitive) magnetic sensor 57 for the measurement of the magnetic signals from the thermo-responsive magnetic nano particles and a drive circuit 58, (2) a cryostat 55 (a container keeping the temperatures low) to keep a SQUID (ultra high sensitive) magnetic sensor 57 to be in low temperatures, (3) a sliding mechanism including a driving motor 53, a wire 52, and a control unit 54, and (4) a magnetic shield box which shields magnetic noises such as earth magnetism, or the like. A drive circuit 58 is used for the purpose to reduce noises.

The samples are mounted on the sliding plate 51, transferred just above the SQUID (ultra high sensitive) magnetic sensor 57 using the sliding mechanism installed outside of the magnetic shield box 56. The magnetic signal when the sample passes through the magnetic sensor 57 is measured and recorded.

Moreover, in order to obtain a larger signal from the thermo-responsive magnetic nano particles, the use of the thermo-responsive magnetic nano particles 71 based on metal oxide or Co (cobalt) metal nano particles as a core may be recommended. Avidin 72 was bound on the surface of these thermo-responsive magnetic nano particles 71, and biotynylated secondary antibody 73 was subsequently bound and labeled in a buffer solution. It was suggested that such a structure made it possible to generate the larger magnetic signal as large as one order of magnitude. In the present invention, buffer solutions were used as a solvent. The present invention is not limited within above embodiments, and various modifications are possible according to the object of the present invention which should not be excluded from the scope of the present invention.

According to the present invention, the thermo-responsive magnetic nano particles have a critical solution temperature across which the particles have a characteristic property to aggregate or to disperse with cooling or heating. Applying this property, for example, by aggregating the additional thermo-responsive magnetic nano particles around one thermo-responsive magnetic nano particle with which an antibody was labeled, the magnetic signal generated from the labeled biopolymer under AC magnetic field may be increased. In the case when the additional thermo-responsive magnetic nano particles are aggregated, a remarkable amplified effect of the magnetic signal was observed as compared with the case when the particles are not aggregated.

The present invention may be applied to the detection of antigen antibody reaction, particularly, as a device for the detection of antigen antibody reaction which increases the efficiency of preparing a slight amount of monoclonal antibody such as enzyme or the like, and also to the DNA chips and microarrays detecting the hybridization of DNA.

What is claimed is:

1. A sensing method for biopolymers by detecting the magnetic signal generated from a labeled biopolymer under AC magnetic field with the use of thermo-responsive magnetic nano particles as label, comprising the steps of;
   using the thermo-responsive magnetic nano particles having a critical solution temperature across which the particles have the ability to aggregate or disperse with cooling or heating;
   binding a ligand for a target biopolymer to said thermo-responsive magnetic nano particles;
   labeling the target biopolymer in solution with said thermo-responsive magnetic nano particles using a biopolymer reaction;
   adding ligand free thermo-responsive magnetic nano particles;
   keeping the solution temperature at which said thermo-responsive magnetic nano particles aggregate;
   applying AC magnetic field after aggregating the thermo-responsive magnetic nano particles and enlarging the aggregate of said thermo-responsive magnetic nano particles; and
   obtaining a larger magnetic signal at the time of measurement as compared with the magnetic signal obtained when said ligand free thermo-responsive magnetic nano particles are not added.

2. The sensing method for biopolymers according to claim 1, wherein;
   binding an antibody for an antigen to said thermo-responsive magnetic nano particles;
   labeling said antigen in solution with the thermo-responsive magnetic nano particles bound with the antibody using an antigen antibody reaction;
   adding the thermo-responsive magnetic nano particles which are not bound with antibody;
   keeping the solution temperature at which said thermo-responsive magnetic nano particles aggregate;
   applying AC magnetic field after aggregating the thermo-responsive magnetic nano particles and enlarging the aggregate of said thermo-responsive magnetic nano particles;
   obtaining a larger magnetic signal at the time of measurement as compared with the magnetic signal obtained when thermo-responsive magnetic nano particles, which are not bound with antibody, are not added; and
   detecting said antibody.

3. The sensing method for biopolymers according to claim 1, wherein;
   labeling a single stranded DNA complementary to a target single stranded DNA with said thermo-responsive magnetic nano particles;
   hybridizing said complementary DNA with said target single stranded DNA in solution;
   adding the thermo-responsive magnetic nano particles which are not labeled with said complementary DNA just before the measurement of magnetic signal;
   keeping the solution temperature at which said thermo-responsive magnetic nano particles aggregate;
   applying AC magnetic field after aggregating the thermo-responsive magnetic nano particles and enlarging the aggregate of said thermo-responsive magnetic nano particles;
   obtaining a larger magnetic signal at the time of measurement as compared with the magnetic signal obtained when the thermo-responsive magnetic nano particles, which are not bound with said complementary DNA, are not added; and
   detecting said target single stranded DNA.

4. The sensing method for biopolymers according to any one of claims 1 to 3, wherein said thermo-responsive magnetic nano particles comprise a thermo-responsive polymer and magnetic nano particles;
   said thermo-responsive polymer is the polymer having a lower critical solution temperature or an upper critical solution temperature;
   said magnetic nano particles are the particles comprising a polyhydric alcohol and a magnetic material;
the polymer having a lower critical solution temperature is the polymer comprising at least one monomer component which is selected from the group consisting of N-n-propylacrylamide, N-isopropylacrylamide, N-ethylacrylamide, N,N-dimethylacrylamide, N-acryloylpyrrolidine, N-acryloylpiperidine, N-acryloylmorpholine, N-n-propylmethacrylamide, N-isopropylmethacrylamide, N-ethylmethacrylamide, N,N-dimethylmethacrylamide, N-methacryloylpyrrolidine, N-methacryloylpiperidine, and N-methacryloylmorpholine;
   the polymer having an upper critical solution temperature is the polymer comprising at least one monomer component which is selected from the group consisting of acrylamide, acetylacrylamide, biotinol acrylate, N-biotinyl-N'-methacryloyltrimethyleneamide, N-acryloylglycinamide, acryloylsarcosinamide, methacryloylsarcosinamide, acryloylnipecotamide, and acryloylmethyluracil; said polyhydric alcohol is at least one alcohol component which is selected from the group consisting of dextran, polyvinyl alcohol, mannnitol, and sorbitol; and
   the magnetic material is at least one kind of material which is selected from the group consisting of oxide magnetic materials and metallic magnetic materials.

5. The sensing method for biopolymers according to claim 4, wherein the thermo-responsive magnetic nano particles comprise a thermo-responsive polymer and magnetic nano particles;
   the thermo-responsive polymer comprising the polymer obtained from N-isopropylacrylamide or from N-acryloylglicinamide; and
   the magnetic nano particles are the particles comprising dextran and ferrite.

* * * * *